(12) United States Patent
Kano et al.

(10) Patent No.: US 10,085,973 B2
(45) Date of Patent: Oct. 2, 2018

(54) PHARMACEUTICAL COMPOSITION CONTAINING A COMPOUND HAVING A THROMBOPOIETIN RECEPTOR AGONISTIC ACTIVITY

(71) Applicant: Shionogi & Co., Ltd., Osaka-shi (JP)

(72) Inventors: Takeshi Kano, Osaka (JP); Takahiro Fukuhara, Osaka (JP); Takayuki Katsube, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 15/210,554

(22) Filed: Jul. 14, 2016

(65) Prior Publication Data

US 2016/0317506 A1   Nov. 3, 2016

Related U.S. Application Data

(62) Division of application No. 14/411,811, filed as application No. PCT/JP2013/067769 on Jun. 28, 2013.

(30) Foreign Application Priority Data

Jun. 29, 2012 (JP) ................. 2012-146230

(51) Int. Cl.
| | |
|---|---|
| *A61K 31/426* | (2006.01) |
| *A61K 9/06* | (2006.01) |
| *A61K 9/08* | (2006.01) |
| *A61K 31/4152* | (2006.01) |
| *A61K 31/4155* | (2006.01) |
| *A61K 31/496* | (2006.01) |

(52) U.S. Cl.
CPC ............ *A61K 31/426* (2013.01); *A61K 9/06* (2013.01); *A61K 9/08* (2013.01); *A61K 31/4152* (2013.01); *A61K 31/4155* (2013.01); *A61K 31/496* (2013.01)

(58) Field of Classification Search
CPC .......... A61K 31/426; A61K 31/4152; A61K 31/4155; A61K 31/496; A61K 9/08; A61K 9/06
See application file for complete search history.

(56) References Cited

U.S. PATENT DOCUMENTS

| 8,530,668 B2 | 9/2013 | Takayama et al. | |
| 8,889,722 B2 | 11/2014 | Takayama et al. | |
| 2011/0166112 A1* | 7/2011 | Zhang ................ | A61K 31/496 514/171 |

FOREIGN PATENT DOCUMENTS

| EP | 2184279 | 5/2010 |
| WO | 0044398 | 8/2000 |
| WO | 2009017098 | 2/2009 |

OTHER PUBLICATIONS

Imbach, P., "Thrombopoietin-receptor agonists for primary immune thrombocytopenia." New England Journal of Medicine 365.8 (2011): 734-741.*
Kawaguchi, T., "Thrombocytopenia, an important interfering factor of antiviral therapy and hepatocellular carcinoma treatment for chronic liver diseases." The Kurume medical journal 56.1+ 2 (2009): 9-15.*
International Search Report and Written Opinion issued in International Application No. PCT/JP2013/067769 dated Aug. 20, 2013 (8 pages).
Preliminary Report issued in International Application No. PCT/JP2013/067769 dated Jan. 8, 2015 (8 pages).
Ligand Pharmaceuticals, Inc., "Investor and Analyst Day,", 2011, 83 pages, website, http://phx.corporate-ir.net.
Afdhal et al.: "Eltrombopag in chronic liver disease patients with thrombocytopenia undergoing an elective invasive procedure: results from Elevate, a randomized clinical trial", Journal of Hepatology, 2010, vol. 52, S460, 1 page.
Vigon et al.: "Molecular cloning and characterization of MPL, the human homolog of the v-mpl oncogene: Identification of a member of the hematopoietic growth factor receptor superfamily" Proc. Natl. Acad. Sci, USA, 1992, vol. 89, pp. 5640-5644.
"A package insert of Romiplate for subcutaneous injection"; Thrombopoiesis-stimulating Agent/Thrombopoietin Receptor Agonist, (Apr. 2011, version 1), Partial English Translation, 6 pages.
A package insert of Revolade tablets; Oral Platelet-booster/Thrombopoietin Receptor Agonist, (Oct. 2010, version 1), Partial English Translation, 7 pages total.

* cited by examiner

*Primary Examiner* — John M Mauro

(74) *Attorney, Agent, or Firm* — Hamre, Schumann, Mueller & Larson, P.C.

(57) ABSTRACT

The present inventor has found out that the following criteria enable to ensure an effect for increasing the platelet count while preventing an excessive increase in the platelet count; "when the platelet count has increased by a certain amount and reached to a sufficient level of the platelet count during administration of a pharmaceutical composition containing a compound having a thrombopoietin receptor agonistic activity, administration of the pharmaceutical composition is discontinued thereafter".

17 Claims, 3 Drawing Sheets

[Fig. 1]

(a) PK Model

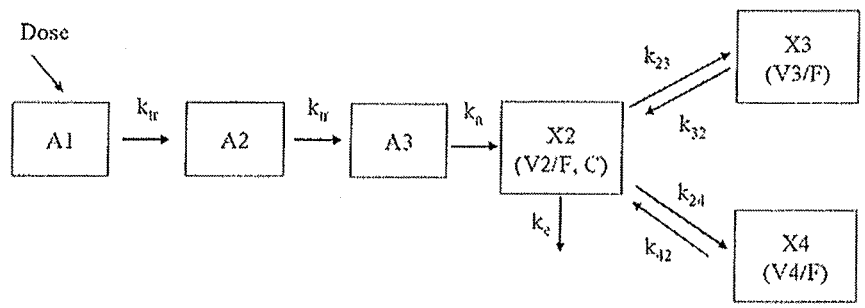

$dA1/dt = -k_{tr}*A1$
$dA2/dt = k_{tr}*A1 - k_{tr}*A2$
$dA3/dt = k_{tr}*A2 - k_a*A3$
$dX2/dt = k_a*A3 - k_{23}*X2 - k_{24}*X2 + k_{32}*X3 + K_{42}*X4 - k_e*X2$
$dX3/dt = k_{23}*X2 - k_{32}*X3$
$dA4/dt = k_{24}*X2 - k_{42}*X4$ $C = X2/(V2/F)$
$CL/F = k_e*V2/F$
$K_{23} = (Q3/F)/(V2/F)$
$K_{32} = (Q3/F)/(V3/F)$
$K_{24} = (Q4/F)/(V2/F)$
$K_{42} = (Q4/F)/(V4/F)$

Initial condition (i.e., t=0)
A1 = Dose
A2 = 0
A3 = 0
X2 = 0
X3 = 0
X4 = 0

(b) PD Model

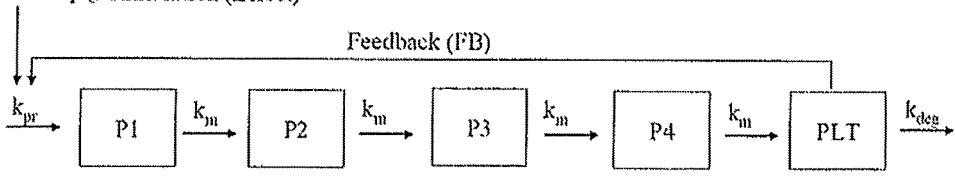

Effect = $E_{max}*C^r/(EC_{50}^r+C^r)$
FB = $(PLT_0/PLT)^\gamma$
$k_{pr} = PLT_0*k_{deg}$
$dP1/dt = k_{pr}*FB*(1+Effect) - k_m*P1$
$dP2/dt = k_m*P1 - k_m*P2$
$dP3/dt = k_m*P2 - k_m*P3$
$dP4/dt = k_m*P3 - k_m*P4$
$dPLT/dt = k_m*P4 - k_{deg}*PLT$ Initial condition (i.e., t=0)
P1 = $k_{pr}/k_m$
P2 = $k_{pr}/k_m$
P3 = $k_{pr}/k_m$
P4 = $k_{pr}/k_m$
PLT = $PLT_0 = k_{pr}/k_{deg}$ C: plasma lusutrombopag concentrations

[Fig. 2]
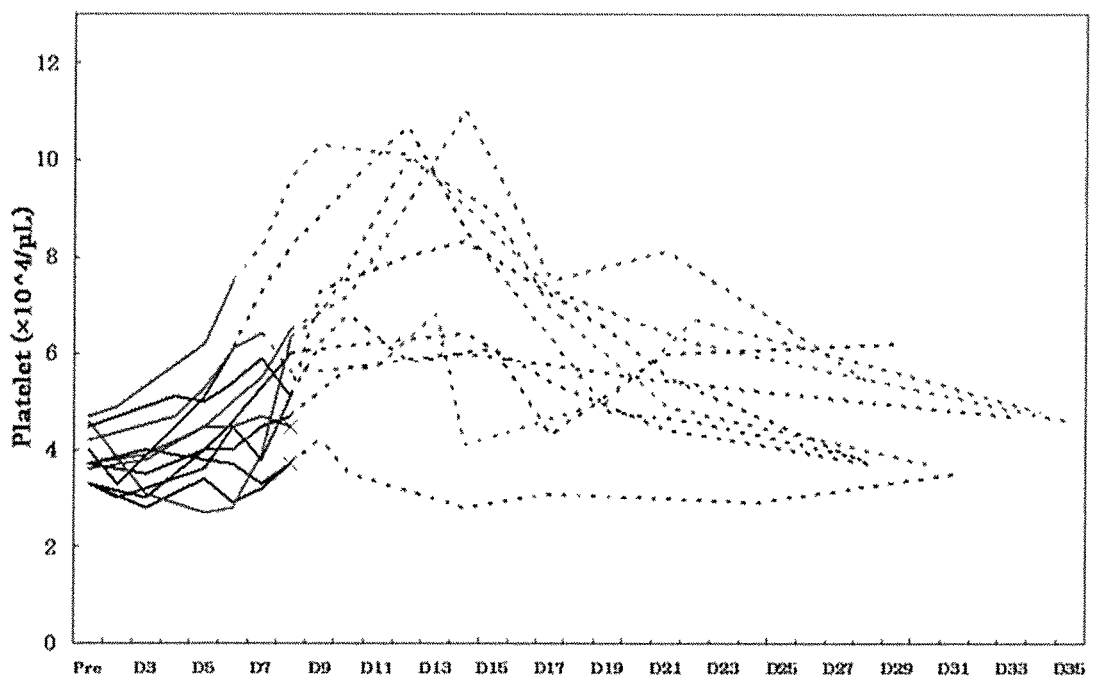
[Fig. 3]
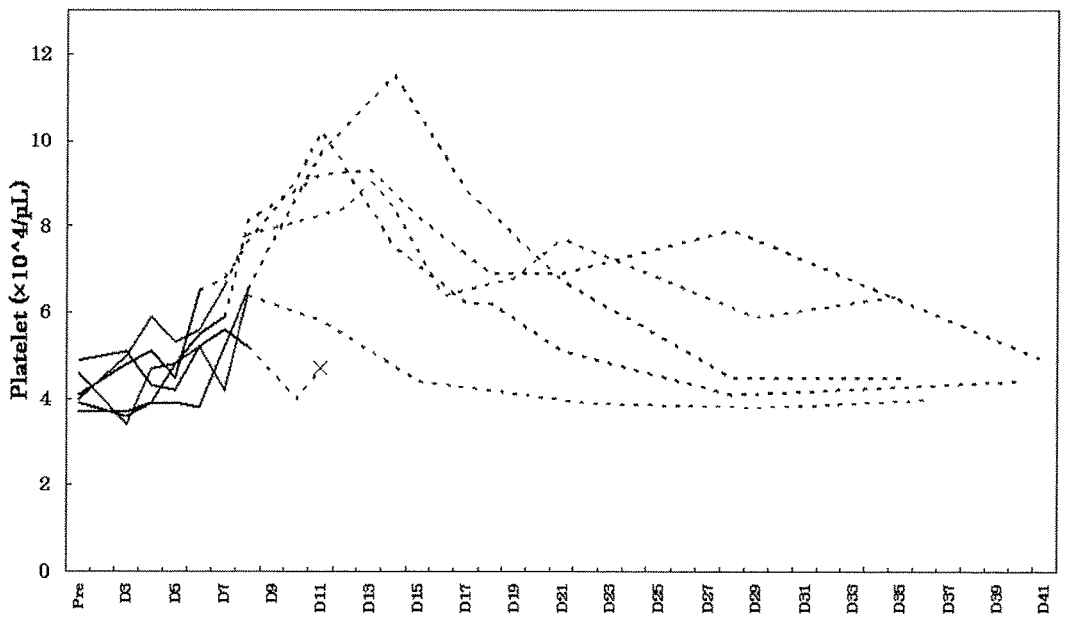

[Fig. 4]
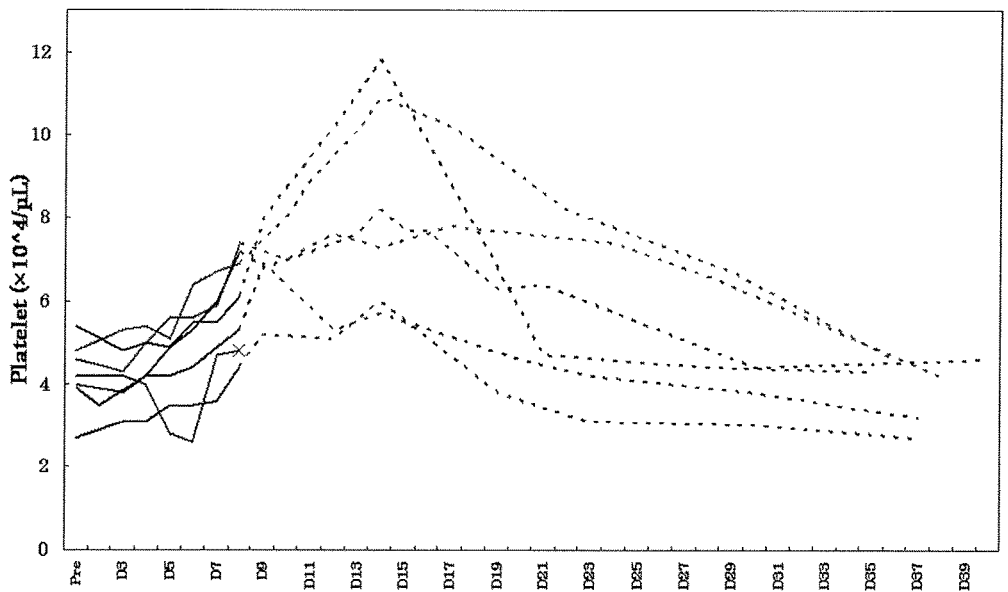
[Fig. 5]
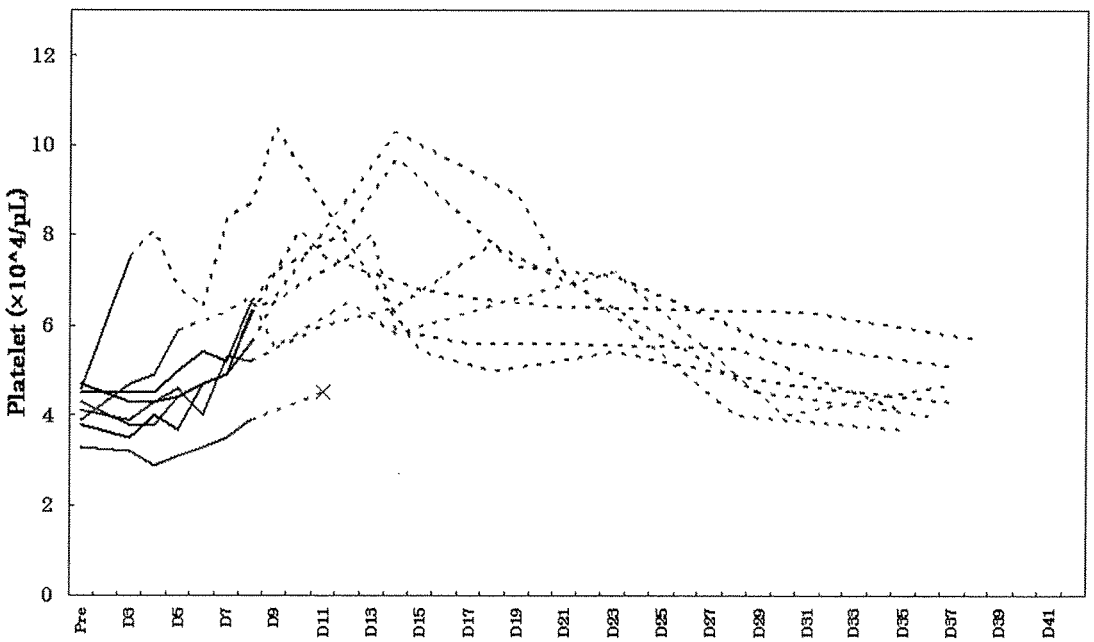

PHARMACEUTICAL COMPOSITION CONTAINING A COMPOUND HAVING A THROMBOPOIETIN RECEPTOR AGONISTIC ACTIVITY

FIELD OF THE INVENTION

The present invention relates to a pharmaceutical composition containing a compound having a thrombopoietin receptor agonistic activity.

BACKGROUND OF THE INVENTION

Thrombocytopenia is a disease in which platelet destruction is promoted or platelets are insufficiently produced, causing a reduction in the number of platelets and resulting in bleeding tendency. Hemorrhagic events include brain hemorrhage, internal hemorrhage, petechia, purpura, mucosal hemorrhages (nasal hemorrhage, gastrointestinal hemorrhage, genital hemorrhage) and the like, and in some cases, excessive bleeding may be observed after surgery.

It is known that one of the causes of thrombocytopenia is chronic liver disease. In chronic liver disease patients, a decrease in hepatic spare ability with the development of disease stages, and a decrease in the platelet count with hypersplenism are observed. Most of chronic hepatitis is caused by hepatitis B or C virus infection, of which hepatitis C virus infection is predominant. Hepatitis C tends to become chronic and is developed to liver cirrhosis and further to hepatocellular carcinoma, causing about 34,000 deaths annually. Upon treatment for hepatitis or liver cancer, patients with thrombocytopenia may not be able to receive anti-virus therapy using interferons or may require splenectomy, partial splenic embolization (PSE) or platelet transfusion when undergoing invasive procedures such as laparotomy and local therapy.

However, these procedures have the following problems, and thus are not always safe and convenient:

splenectomy is highly invasive and is reported to cause portal vein thrombosis and decrease immunocompetence;

PSE is reported to cause splenic abscess and sepsis;

platelet transfusion has risks of transfusion-related side effects (transfusion-related acute lung injury and infection), and platelet products have a short expiration date (4 days after blood collection). It is also known that repeated platelet transfusion may promote antibody production, causing platelet transfusion refractoriness.

Under these circumstances, there is a need for a therapeutic agent for thrombocytopenia that has no side effect and can be readily administered.

Thrombopoietin (TPO) is a cytokine that acts on hematopoietic stem cells/megakaryocyte progenitor cells to promote proliferation and differentiation to megakaryocytes and production of platelets. A recombinant human TPO was previously studied in a clinical trial. However, it induced a neutralizing antibody directed to endogenous TPO, and thus the development thereof was stopped due to antigenicity. Among cytokines having activity on production of platelets in megakaryocytes, only an injection containing interleukin 11 is clinically applied in the United States. However, the approved indication thereof is limited to improvement of thrombocytopenia caused by bone-marrow suppression after chemotherapy because of side effects including fluid accumulation, palpitation, edema and the like.

A nucleotide sequence of a gene encoding the thrombopoietin receptor is disclosed in Non-Patent Document 1.

Under these circumstances, compounds having a thrombopoietin receptor agonistic activity are expected as therapeutic agents for thrombocytopenia that can replace the present therapies and treatments including platelet transfusion. As therapeutic agents for chronic immune thrombocytopenia (chronic ITP), romiplostim which is an injectable thrombopoietin mimetic peptide and eltrombopag which is a low molecular TPO receptor agonist are currently approved in the United States and Europe.

Patent Document 1 discloses, as a compound having a thrombopoietin receptor agonistic activity,
(E)-3-[2,6-dichloro-4-[4-[3-[(S)-1-hexyloxyethyl]-2-methoxyphenyl]-thiazol-2-ylcarbamoyl]-phenyl]-2-methylacrylic acid.

Eltrombopag, a low molecular compound having a thrombopoietin receptor agonistic activity, was studied in a clinical trial abroad designed to administer the investigational drug for 2 weeks before the invasive procedures to chronic liver disease patients who were scheduled to undergo invasive procedures and had a platelet count of less than $5 \times 10^4/\mu L$ and the Child-Pugh score of 12 or less. The results showed that an avoidance of platelet transfusion, an efficacy endpoint, was higher in the active drug group than in the placebo group (placebo group: 19%, active drug group: 72%). However, the incidence of portal vein thrombosis was higher in the active drug group than in the placebo group (placebo group: 1%, active drug group: 4%). It is reported in Non-Patent Document 2 that most cases of portal vein thrombosis were developed after invasive procedures carried out after termination of administration of the investigational drug and that the platelet count in 5 cases out of 6 in the active drug group was $20 \times 10^4/\mu L$ or higher at the time of the development of portal vein thrombosis. With regard to the correlation between the risk of development of portal vein thrombosis and the platelet count, the risk in the group having the platelet count of $20 \times 10^4/\mu L$ or higher during the investigation period was about 9 times higher than the risk in the group with the platelet count of less than $20 \times 10^4/\mu L$ (10.6% vs. 1.2%). Thus it is suggested that an increase in the platelet count in patients having thrombocytopenia resulting from development of chronic hepatitis to $20 \times 10^4/\mu L$ or higher may increase the risk of onset of portal vein thrombosis.

Compounds having a thrombopoietin receptor agonistic activity, eltrombopag and romiplostim, have already been launched for the indication of "chronic idiopathic thrombocytopenic purpura". The administration discontinuating criteria of the drugs upon excessive increase in the platelet count indicated in the package inserts of the drugs (Non-Patent Document 3 and 4) is "stop the drug if the platelet count exceeds $400,000/\mu L$".

PRIOR ART REFERENCES

Patent Document 1

International Publication WO 2009/017098

Non-Patent Document 1

Proceedings of the National Academy of Sciences of the United States of America (Proc. Natl. Acad. Sci. USA) 1992, vol. 89, p. 5640-5644

Non-Patent Document 2

Ligand Pharmaceuticals, Inc., "Eltrombopag in Chronic Liver Disease Patients with Thrombocytopenia Undergoing an Elective Invasive Procedure: Results from ELEVATE, a Randomised Clinical Trial." <Internet URL: http://phx.corporate-ir.net/External.File?item=UGFyZW50SUQ9NDMxMzY4fENoaWxkSUQ9NDQ5NjIwfFR5cGU9MQ==&t=1>

Non-Patent Document 3

A package insert of Romiplate (trade name) for subcutaneous injection (250 mg; general name: romiplostim) (April 2011, version 1), Kyowa Hakko Kirin Co., Ltd.

Non-Patent Document 4

A package insert of Revolade (trade name) tablets (12.5 mg and 25 mg; general name: eltrombopag) (October 2010, version 1), GlaxoSmithKline K.K.

SUMMARY OF THE INVENTION

Problems to be Solved by the Invention

It is difficult for conventional pharmaceutical compositions containing a compound having a thrombopoietin receptor agonistic activity to both increase the platelet count to a sufficient level and avoid an excessive increase in the platelet count.

Thus the purpose of the present invention is to provide a pharmaceutical composition containing a compound having a thrombopoietin receptor agonistic activity that enable to both increase the platelet count to a sufficient level and avoid an excessive increase in the platelet count.

Means for Solving the Problem

The present inventor has found out that the following criteria enable to ensure an effect for increasing the platelet count while preventing an excessive increase in the platelet count; "when the platelet count has increased by a certain amount and has reached to a sufficient level of the platelet count during administration of a pharmaceutical composition containing a compound having a thrombopoietin receptor agonistic activity, administration of the pharmaceutical composition is discontinued thereafter".

Thus the present invention relates to the following points:

(1) A pharmaceutical composition for increasing platelets containing a compound having a thrombopoietin receptor agonistic activity, characterized by discontinuing administration of the pharmaceutical composition to a patient at the time point when a platelet count in the patient has increased by $2\times10^4/\mu L$ or more from a platelet count before initiation of administration and has reached to $5\times10^4/\mu L$ or higher.

(2) The pharmaceutical composition according to (1), which is administered to a thrombocytopenia patient.

(3) The pharmaceutical composition according to (1) or (2), wherein the platelet count in the patient before initiation of administration of the pharmaceutical composition is less than $5\times10^4/\mu L$.

(4) The pharmaceutical composition according to (2) or (3), wherein the patient is scheduled to undergo invasive procedures.

(5) The pharmaceutical composition according to (4), wherein the invasive procedures are elective invasive procedures.

(6) The pharmaceutical composition according to (4) or (5), wherein the invasive procedures are radiofrequency ablation.

(7) The pharmaceutical composition according to (6), wherein the radiofrequency ablation is performed on liver cancer.

(8) The pharmaceutical composition according to (7), wherein the liver cancer is primary liver cancer.

(9) The pharmaceutical composition according to any of (1) to (8), wherein the patient has chronic liver disease.

(10) The pharmaceutical composition according to (9), wherein the chronic liver disease is caused by hepatitis B virus or hepatitis C virus.

(11) The pharmaceutical composition according to any of (1) to (10), wherein the compound having a thrombopoietin receptor agonistic activity is (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

(12) The pharmaceutical composition according to (11), which is orally administered.

(13) The pharmaceutical composition according to (12), which is administered at 2.0 to 4.0 mg/day as an amount of (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

(14) The pharmaceutical composition according to (13), wherein a maximum administration period with once daily administration is 14 days or less.

(15) The pharmaceutical composition according to (1), for promoting production of platelets before invasive procedures in thrombocytopenic patients with chronic liver disease.

(16) The pharmaceutical composition according to (1), for promoting production of platelets before elective invasive procedures in thrombocytopenic patients with chronic liver disease.

(17) The pharmaceutical composition according to (1), for promoting production of platelets before local therapy for primary liver cancer.

(18) The pharmaceutical composition according to (1), for promoting production of platelets before radiofrequency ablation for primary liver cancer.

(19) The pharmaceutical composition according to (1), for promoting production of platelets before various minimally invasive procedures in thrombocytopenic patients with chronic liver disease.

(20) A method for increasing platelets comprising the steps of: administering a pharmaceutical composition containing a compound having a thrombopoietin receptor agonistic activity to a patient; and discontinuing administration at the time point when a platelet count in the patient has increased by $2\times10^4/\mu L$ or more from a platelet count before initiation of administration and has reached to $5\times10^4/\mu L$ or higher.

(21) Use of a compound having a thrombopoietin receptor agonistic activity for increasing platelets, characterized by discontinuing administration of the compound to a patient at the time point when a platelet count in the patient has increased by $2\times10^4/\mu L$ or more from a platelet count before initiation of administration and has reached to $5\times10^4/\mu L$ or higher.

(1A) A method for increasing platelets comprising the steps of:
administering a pharmaceutical composition containing a compound having a thrombopoietin receptor agonistic activity to a patient; and
discontinuing administration at the time point when a platelet count in the patient has increased by $2\times10^4/\mu L$ or more from a platelet count before initiation of administration and has reached to $5\times10^4/\mu L$ or higher.

(2A) The method for increasing platelets according to (1A), wherein the patient has thrombocytopenia.

(3A) The method for increasing platelets according to (1A) or (2A), wherein the platelet count in the patient before initiation of administration of the pharmaceutical composition is less than $5\times10^4/\mu L$.

(4A) The method for increasing platelets according to (2A) or (3A), wherein the patient is scheduled to undergo invasive procedures.

(5A) The method for increasing platelets according to (4A), wherein the invasive procedures are elective invasive procedures.

(6A) The method for increasing platelets according to (4A) or (5A), wherein the invasive procedures are radiofrequency ablation.

(7A) The method for increasing platelets according to (6A), wherein the radiofrequency ablation is performed on liver cancer.

(8A) The method for increasing platelets according to (7A), wherein the liver cancer is primary liver cancer.

(9A) The method for increasing platelets according to any of (1A) to (8A), wherein the patient has chronic liver disease.

(10A) The method for increasing platelets according to (9A), wherein the chronic liver disease is caused by hepatitis B virus or hepatitis C virus.

(11A) The method for increasing platelets according to any of (1A) to (10A), wherein the compound having a thrombopoietin receptor agonistic activity is (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

(12A) The method for increasing platelets according to (11A), wherein the pharmaceutical composition is orally administered.

(13A) The method for increasing platelets according to (12A), wherein the pharmaceutical composition is administered at 2.0 to 4.0 mg/day as an amount of (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

(14A) The method for increasing platelets according to (13A), wherein a maximum administration period with once daily administration is 14 days or less.

(15A) The method for increasing platelets according to (1A), for promoting production of platelets before invasive procedures in thrombocytopenic patients with chronic liver disease.

(16A) The method for increasing platelets according to (1A), for promoting production of platelets before elective invasive procedures in thrombocytopenic patients with chronic liver disease.

(17A) The method for increasing platelets according to (1A), for promoting production of platelets before local therapy for primary liver cancer.

(18A) The method for increasing platelets according to (1A), for promoting production of platelets before radiofrequency ablation for primary liver cancer.

(19A) The method for increasing platelets according to (1A), for promoting production of platelets before various minimally invasive procedures in thrombocytopenic patients with chronic liver disease.

(1B) A compound having a thrombopoietin receptor agonistic activity for use in increasing platelets, characterized by discontinuing administration of the compound to a patient at the time point when a platelet count in the patient has increased by $2\times10^4/\mu L$ or more from a platelet count before initiation of administration and has reached to $5\times10^4/\mu L$ or higher.

(2B) The compound according to (1B), which is administered to a thrombocytopenia patient.

(3B) The compound according to (1B) or (2B), wherein the platelet count in the patient before initiation of administration of the compound is less than $5\times10^4/\mu L$.

(4B) The compound according to (2B) or (3B), wherein the patient is scheduled to undergo invasive procedures.

(5B) The compound according to (4B), wherein the invasive procedures are elective invasive procedures.

(6B) The compound according to (4B) or (5B), wherein the invasive procedures are radiofrequency ablation.

(7B) The compound according to (6B), wherein the radiofrequency ablation is performed on liver cancer.

(8B) The compound according to (7B), wherein the liver cancer is primary liver cancer.

(9B) The compound according to any of (1B) to (8B), wherein the patient has chronic liver disease.

(10B) The compound according to (9B), wherein the chronic liver disease is caused by hepatitis B virus or hepatitis C virus.

(11B) The compound according to any of (1B) to (10B), wherein the compound having a thrombopoietin receptor agonistic activity is (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

(12B) The compound according to (11B), which is orally administered.

(13B) The compound according to (12B), which is administered at 2.0 to 4.0 mg/day as an amount of (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

(14B) The compound according to (13B), wherein a maximum administration period with once daily administeration is 14 days or less.

(15B) The compound according to (1B), for promoting production of platelets before invasive procedures in thrombocytopenic patients with chronic liver disease.

(16B) The compound according to (1B), for promoting production of platelets before elective invasive procedures in thrombocytopenic patients with chronic liver disease.

(17B) The compound according to (1B), for promoting production of platelets before local therapy for primary liver cancer.

(18B) The compound according to (1B), for promoting production of platelets before radiofrequency ablation for primary liver cancer.

(19B) The compound according to (1B), for promoting production of platelets before various minimally invasive procedures in thrombocytopenic patients with chronic liver disease.

(1C) Use of a compound having a thrombopoietin receptor agonistic activity for manufacturing a medicament for increasing platelets, characterized by discontinuing administration of the medicament to a patient at the time point when a platelet count in the patient has increased by $2\times10^4/\mu L$ or more from a platelet count before initiation of administration and has reached to $5\times10^4/\mu L$ or higher.

(2C) Use of a compound according to (1C), wherein the medicament is administered to a thrombocytopenia patient.

(3C) Use of a compound according to (1C) or (2C), wherein the platelet count in the patient before initiation of administration of the medicament is less than $5\times10^4/\mu L$.

(4C) Use of a compound according to (2C) or (3C), wherein the patient is scheduled to undergo invasive procedures.

(5C) Use of a compound according to (4C), wherein the invasive procedures are elective invasive procedures.

(6C) Use of a compound according to (4C) or (5C), wherein the invasive procedures are radiofrequency ablation.

(7C) Use of a compound according to (6C), wherein the radiofrequency ablation is performed on liver cancer.

(8C) Use of a compound according to (7C), wherein the liver cancer is primary liver cancer.

(9C) Use of a compound according to any of (1C) to (8C), wherein the patient has chronic liver disease.

(10C) Use of a compound according to (9C), wherein the chronic liver disease is caused by hepatitis B virus or hepatitis C virus.

(11C) Use of a compound according to any of (1C) to (10C), wherein the compound having a thrombopoietin receptor agonistic activity is (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

(12C) Use of a compound according to (11C), wherein the medicament is orally administered.

(13C) Use of a compound according to (12C), wherein the medicament is administered at 2.0 to 4.0 mg/day as an amount of (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

(14C) Use of a compound according to (13C), wherein a maximum administration period with once daily administration is 14 days or less.

(15C) Use of a compound according to (1C), for promoting production of platelets before invasive procedures in thrombocytopenic patients with chronic liver disease.

(16C) Use of a compound according to (1C), for promoting production of platelets before elective invasive procedures in thrombocytopenic patients with chronic liver disease.

(17C) Use of a compound according to (1C), for promoting production of platelets before local therapy for primary liver cancer.

(18C) Use of a compound according to (1C), for promoting production of platelets before radiofrequency ablation for primary liver cancer.

(19C) Use of a compound according to (1C), for promoting production of platelets before various minimally invasive procedures in thrombocytopenic patients with chronic liver disease.

The present invention further includes the following embodiments of the above points (1) to (21), (1A) to (19A), (1B) to (19B) and (1C) to (19C), wherein "$2\times10^4/\mu L$" and "$5\times10^4/\mu L$" are regarded as "a pre-defined level of platelet count increment" and "a pre-defined level of platelet count", respectively:

(1') A pharmaceutical composition for increasing platelets containing a compound having a thrombopoietin receptor agonistic activity, discontinuing administration of the pharmaceutical composition to a patient at the time point when a platelet count in the patient has increased by a pre-defined level of platelet count increment or more from a platelet count before initiation of administration and has reached to a pre-defined level of platelet count or higher.

(2') The pharmaceutical composition according to (1'), which is administered to a thrombocytopenia patient.

(3') The pharmaceutical composition according to (1') or (2'), wherein the platelet count in the patient before initiation of administration of the pharmaceutical composition is less than the pre-defined level of platelet count.

(4') The pharmaceutical composition according to (2') or (3'), wherein the patient is scheduled to undergo invasive procedures.

(5') The pharmaceutical composition according to (4'), wherein the invasive procedures are elective invasive procedures.

(6') The pharmaceutical composition according to (4') or (5'), wherein the invasive procedures are radiofrequency ablation.

(7') The pharmaceutical composition according to (6'), wherein the radiofrequency ablation is performed on liver cancer.

(8') The pharmaceutical composition according to (7'), wherein the liver cancer is primary liver cancer.

(9') The pharmaceutical composition according to any of (1') to (8'), wherein the patient has chronic liver disease.

(10') The pharmaceutical composition according to (9'), wherein the chronic liver disease is caused by hepatitis B virus or hepatitis C virus.

(11') The pharmaceutical composition according to any of (1') to (10'), wherein the compound having a thrombopoietin receptor agonistic activity is (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

(12') The pharmaceutical composition according to (11'), which is orally administered.

(13') The pharmaceutical composition according to (12'), which is administered at 2.0 to 4.0 mg/day as an amount of (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

(14') The pharmaceutical composition according to (13'), wherein a maximum administration period with once daily administration is 14 days or less.

(15') The pharmaceutical composition according to (1'), for promoting production of platelets before invasive procedures in thrombocytopenic patients with chronic liver disease.

(16') The pharmaceutical composition according to (1'), for promoting production of platelets before elective invasive procedures in thrombocytopenic patients with chronic liver disease.

(17') The pharmaceutical composition according to (1'), for promoting production of platelets before local therapy for primary liver cancer.

(18') The pharmaceutical composition according to (1'), for promoting production of platelets before radiofrequency ablation for primary liver cancer.

(19') The pharmaceutical composition according to (1'), for promoting production of platelets before various minimally invasive procedures in thrombocytopenic patients with chronic liver disease.

(20') A method for increasing platelets comprising the steps of:

administering a pharmaceutical composition containing a compound having a thrombopoietin receptor agonistic activity to a patient; and discontinuing administration at the time point when a platelet count in the patient has increased by a pre-defined level of platelet count increment or more from a platelet count before initiation of administration and has reached to a pre-defined level of platelet count or higher.

(21') Use of a compound having a thrombopoietin receptor agonistic activity for increasing platelets, characterized by discontinuing administration of the compound to a patient at the time point when a platelet count in the patient has increased by a pre-defined level of platelet count increment or more from a platelet count before initiation of administration and has reached to a pre-defined level of platelet count or higher.

(1A') A method for increasing platelets comprising the steps of:
administering a pharmaceutical composition containing a compound having a thrombopoietin receptor agonistic activity to a patient; and
discontinuing administration at the time point when a platelet count in the patient has increased by a pre-defined level of platelet count increment or more from a platelet count before initiation of administration and has reached to a pre-defined level of platelet count or higher.

(2A') The method for increasing platelets according to (1A'), wherein the patient has thrombocytopenia.

(3A') The method for increasing platelets according to (1A') or (2A'), wherein the platelet count in the patient before initiation of administration of the pharmaceutical composition is less than the pre-defined level of platelet count.

(4A') The method for increasing platelets according to (2A') or (3A'), wherein the patient is scheduled to undergo invasive procedures.

(5A') The method for increasing platelets according to (4A'), wherein the invasive procedures are elective invasive procedures.

(6A') The method for increasing platelets according to (4A') or (5A'), wherein the invasive procedures are radiofrequency ablation.

(7A') The method for increasing platelets according to (6A'), wherein the radiofrequency ablation is performed on liver cancer.

(8A') The method for increasing platelets according to (7A'), wherein the liver cancer is primary liver cancer.

(9A') The method for increasing platelets according to any of (1A') to (8A'), wherein the patient has chronic liver disease.

(10A') The method for increasing platelets according to (9A'), wherein the chronic liver disease is caused by hepatitis B virus or hepatitis C virus.

(11A') The method for increasing platelets according to any of (1A') to (10A'), wherein the compound having a thrombopoietin receptor agonistic activity is (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

(12A') The method for increasing platelets according to (11A'), wherein the pharmaceutical composition is orally administered.

(13A') The method for increasing platelets according to (12A'), wherein the pharmaceutical composition is administered at 2.0 to 4.0 mg/day as an amount of (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

(14A') The method for increasing platelets according to (13A), wherein a maximum administration period with once daily administration is 14 days or less.

(15A') The method for increasing platelets according to (1A'), for promoting production of platelets before invasive procedures in thrombocytopenic patients with chronic liver disease.

(16A') The method for increasing platelets according to (1A'), for promoting production of platelets before elective invasive procedures in thrombocytopenic patients with chronic liver disease.

(17A') The method for increasing platelets according to (1A'), for promoting production of platelets before local therapy for primary liver cancer.

(18A') The method for increasing platelets according to (1A'), for promoting production of platelets before radiofrequency ablation for primary liver cancer.

(19A') The method for increasing platelets according to (1A'), for promoting production of platelets before various minimally invasive procedures in thrombocytopenic patients with chronic liver disease.

(1B') A compound having a thrombopoietin receptor agonistic activity for use in increasing platelets, characterized by discontinuing administration of the compound to a patient at the time point when a platelet count in the patient has increased by a pre-defined level of platelet count increment or more from a platelet count before initiation of administration and has reached to a pre-defined level of platelet count or higher.

(2B') The compound according to (1B'), which is administered to a thrombocytopenia patient.

(3B') The compound according to (1B') or (2B'), wherein the platelet count in the patient before initiation of administration of the compound is less than the pre-defined level of platelet count.

(4B') The compound according to (2B') or (3B'), wherein the patient is scheduled to undergo invasive procedures.

(5B') The compound according to (4B'), wherein the invasive procedures are elective invasive procedures.

(6B') The compound according to (4B') or (5B'), wherein the invasive procedures are radiofrequency ablation.

(7B') The compound according to (6B'), wherein the radiofrequency ablation is performed on liver cancer.

(8B') The compound according to (7B'), wherein the liver cancer is primary liver cancer.

(9B') The compound according to any of (1B') to (8B'), wherein the patient has chronic liver disease.

(10B') The compound according to (9B'), wherein the chronic liver disease is caused by hepatitis B virus or hepatitis C virus.

(11B') The compound according to any of (1B') to (10B'), wherein the compound having a thrombopoietin receptor agonistic activity is (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

(12B') The compound according to (11B'), which is orally administered.

(13B') The compound according to (12B'), which is administered at 2.0 to 4.0 mg/day as an amount of (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

(14B') The compound according to (13B'), wherein a maximum administration period with once daily administration is 14 days or less.

(15B') The compound according to (1B'), for promoting production of platelets before invasive procedures in thrombocytopenic patients with chronic liver disease.

(16B') The compound according to (1B'), for promoting production of platelets before elective invasive procedures in thrombocytopenic patients with chronic liver disease.

(17B') The compound according to (1B'), for promoting production of platelets before local therapy for primary liver cancer.

(18B') The compound according to (1B'), for promoting production of platelets before radiofrequency ablation for primary liver cancer.

(19B') The compound according to (1B'), for promoting production of platelets before various minimally invasive procedures in thrombocytopenic patients with chronic liver disease.

(1C) Use of a compound having a thrombopoietin receptor agonistic activity for manufacturing a medicament for increasing platelets, characterized by discontinuing administration of the medicament to a patient at the time point when a platelet count in the patient has increased by a pre-defined level of platelet count increment or more from a platelet count before initiation of administration and has reached to a pre-defined level of platelet count or higher.

(2C') Use of a compound according to (1C), wherein the medicament is administered to a thrombocytopenia patient.

(3C') Use of a compound according to (1C') or (2C'), wherein the platelet count in the patient before initiation of administration of the medicament is less than the pre-defined level of platelet count.

(4C') Use of a compound according to (2C') or (3C'), wherein the patient is scheduled to undergo invasive procedures.

(5C') Use of a compound according to (4C'), wherein the invasive procedures are elective invasive procedures.

(6C') Use of a compound according to (4C') or (5C'), wherein the invasive procedures are radiofrequency ablation.

(7C') Use of a compound according to (6C'), wherein the radiofrequency ablation is performed on liver cancer.

(8C') Use of a compound according to (7C'), wherein the liver cancer is primary liver cancer.

(9C') Use of a compound according to any of (1C') to (8C'), wherein the patient has chronic liver disease.

(10C') Use of a compound according to (9C'), wherein the chronic liver disease is caused by hepatitis B virus or hepatitis C virus.

(11C') Use of a compound according to any of (10') to (10C'), wherein the compound having a thrombopoietin receptor agonistic activity is (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

(12C') Use of a compound according to (11C'), wherein the medicament is orally administered.

(13C') Use of a compound according to (12C'), wherein the medicament is administered at 2.0 to 4.0 mg/day as an amount of (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

(14C') Use of a compound according to (13C'), wherein a maximum administration period with once daily administration is 14 days or less.

(15C') Use of a compound according to (1C'), for promoting production of platelets before invasive procedures in thrombocytopenic patients with chronic liver disease.

(16C') Use of a compound according to (1C'), for promoting production of platelets before elective invasive procedures in thrombocytopenic patients with chronic liver disease.

(17C') Use of a compound according to (1C'), for promoting production of platelets before local therapy for primary liver cancer.

(18C') Use of a compound according to (1C'), for promoting production of platelets before radiofrequency ablation for primary liver cancer.

(19C') Use of a compound according to (1C'), for promoting production of platelets before various minimally invasive procedures in thrombocytopenic patients with chronic liver disease.

Effect of the Invention

The pharmaceutical composition having a thrombopoietin receptor agonistic activity according to the present invention is useful because it can increase platelets while avoiding a risk of thrombosis due to an excessive increase in the platelet count.

BRIEF DESCRIPTION OF THE DRAWINGS

FIG. 1 is an illustrative figure showing a schematic view of a PK/PD model with the mass balance equation thereof;

FIG. 2 shows the time course of the platelet count in each patient receiving 2 mg/day of lusutrombopag (n=12). The y-axis shows the platelet count ($\times 10^4/\mu L$), and the x-axis shows the number of days after initiation of administration. Pre means day 1 of administration, and for example D3 means day 3 of administration. The solid line shows the profile of the platelet count during administration of lusutrombopag, and the dotted line shows the profile of the platelet count after termination of administration. For example, when the platelet count, which is measured before administration in day 3, reached the administration discontinuating criteria and thus administration was discontinued, the result is shown with the solid line until D3 and with the dotted line at or after D3. When the platelet count did not reach to the administration discontinuating criteria until day 7 of administration, the result is shown with the solid line until D8 and with the dotted line at or after D8. The symbol x indicates the time point when the platelet transfusion was carried out and the study thereafter was discontinued in the patient (Example 2);

FIG. 3 shows the time course of the platelet count in each patient receiving 2.5 mg/day of lusutrombopag (n=6). The y-axis shows the platelet count ($\times 10^4/\mu L$), and the x-axis shows the number of days after initiation of administration. Pre means day 1 of administration, and for example D3 means day 3 of administration. The solid line shows the profile of the platelet count during administration of lusutrombopag, and the dotted line shows the profile of the platelet count after termination of administration. For example, when the platelet count, which is measured before administration in day 3, reached the administration discontinuating criteria and thus administration was discontinued, the result is shown with the solid line until D3 and with the dotted line at or after D3. When the platelet count did not reach to the administration discontinuating criteria until day 7 of administration, the result is shown with the solid line until D8 and with the dotted line at or after D8. The symbol x indicates the time point when the platelet transfusion was carried out and the study thereafter was discontinued in the patient (Example 2);

FIG. 4 shows the time course of the platelet count in each patient receiving 3 mg/day of lusutrombopag (n=7). The y-axis shows the platelet count ($\times 10^4/\mu L$), and the x-axis shows the number of days after initiation of administration. Pre means day 1 of administration, and for example D3 means day 3 of administration. The solid line shows the profile of the platelet count during administration of lusutrombopag and the dotted line shows the profile of the platelet count after termination of administration. For example, when the platelet count, which is measured before administration in day 3, reached the administration discontinuating criteria and thus administration was discontinued, the result is shown with the solid line until D3 and with the dotted line at or after D3. When the platelet count did not reach to the administration discontinuating criteria until day 7 of administration, the result is shown with the solid line until D8 and with the dotted line at or after D8. The symbol x indicates the time point when the platelet transfusion was carried out and the study thereafter was discontinued (Example 2); and FIG. 5 shows the time course of the platelet count in each patient receiving 4 mg/day of lusutrombopag (n=8). The y-axis shows the platelet count ($\times 10^4/\mu L$), and the x-axis shows the number of days after initiation of administration. Pre means day 1 of administration, and for example D3 means day 3 of administration. The solid line shows the profile of the platelet count during administration of lusutrombopag, and the dotted line shows the profile of the platelet count after termination of administration. For example, when the platelet count, which is measured before administration in day 3, reached the administration discontinuating criteria and thus administration was discontinued, the result is shown with the solid line until D3 and with the dotted line at or after D3. When the platelet count did not reach to the administration discontinuating criteria until day 7 of administration, the result is shown with the solid line until D8 and with the dotted line at or after D8. The symbol x indicates the time point when the platelet transfusion was carried out and the study thereafter was discontinued (Example 2).

MODE FOR CARRYING OUT THE INVENTION

The meanings of the terms used in the present specification are described hereinafter. Each term has the same meaning when it is used alone or in combination with other terms unless otherwise stated.

The term "thrombopoietin receptor agonistic activity" means a function that the object has an affinity towards the thrombopoietin receptor and the substance acts like thrombopoietin.

A compound having a thrombopoietin receptor agonistic activity includes a low molecular compound and protein having a thrombopoietin receptor agonistic activity. Any compound having a thrombopoietin receptor agonistic activity, its pharmaceutically acceptable salt or a solvate thereof can be widely used. The following examples are not intended to limit the compounds. The compounds include compounds disclosed in JP-A No. H10-72492, International Publication WO 96/40750, JP-A No. H11-1477, JP-A No. H11-152276, International Publication WO 00/35446, JP-A No. H10-287634, International Publication WO 01/07423, International Publication WO 01/53267, International Publication WO 02/059099, International Publication WO 02/059100, International Publication WO 02/062775, International Publication WO 2003/062233, International Publication WO 2004/029049, International Publication WO 2005/007651, International Publication WO 2005/014561, JP-A No. 2005-47905, JP-A No. 2006-219480, JP-A No. 2006-219481, International Publication WO 2007/004038, International Publication WO 2007/036709, International Publication WO 2007/054783, International Publication WO 2009/017098 and the like. More specifically, the compound includes lusutrombopag, eltrombopag, avatrombopag, totrombopag and romiplostim. Lusutrombopag, its pharmaceutically acceptable salt or a solvate thereof is particularly preferred and lusutrombopag is still more preferred.

Lusutrombopag is a low molecular human thrombopoietin receptor agonist. The chemical formula of lusutrombopag is "(E)-3-[2,6-dichloro-4-[4-[3-[(S)-1-hexyloxyethyl]-2-methoxyphenyl]-thiazol-2-ylcarbamoyl]-phenyl]-2-methylacrylic acid". Lusutrombopag is represented by the following chemical structural formula:

[Chemical formula 1]

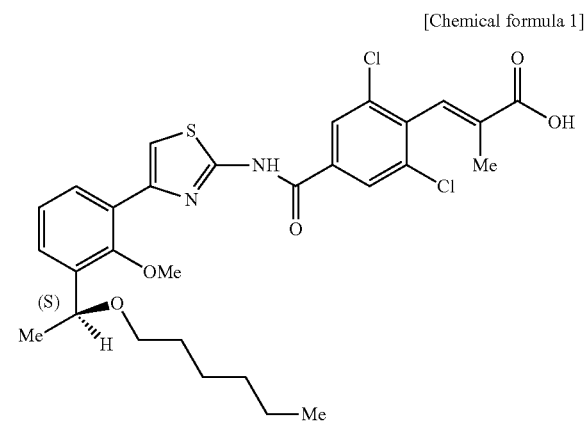

Eltrombopag is represented by the following chemical structural formula:

[Chemical formula 2]

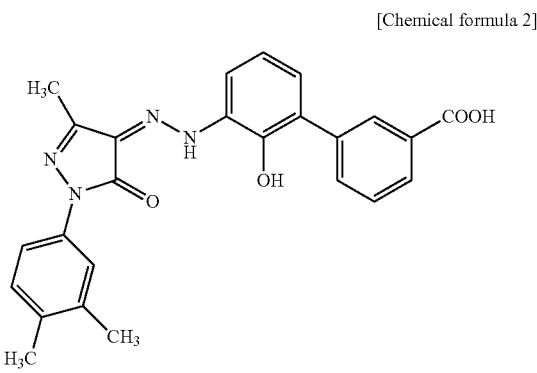 [SMILES: CC1=NN(c2ccc(C)c(C)c2)C(=O)/C1=N\Nc1cccc(-c2cccc(C(=O)O)c2)c1O]

Avatrombopag is represented by the following chemical structural formula:

[Chemical formula 3]

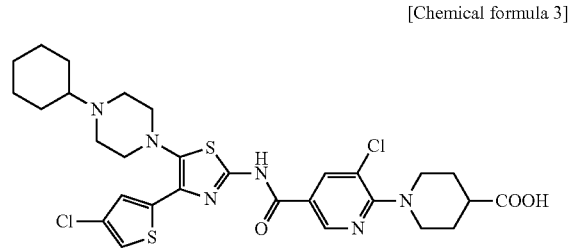 [SMILES: O=C(Nc1nc(-c2cc(Cl)cs2)c(N2CCN(C3CCCCC3)CC2)s1)c1cnc(N2CCC(C(=O)O)CC2)c(Cl)c1]

Totrombopag choline is represented by the following chemical structural formula:

[Chemical formula 4]

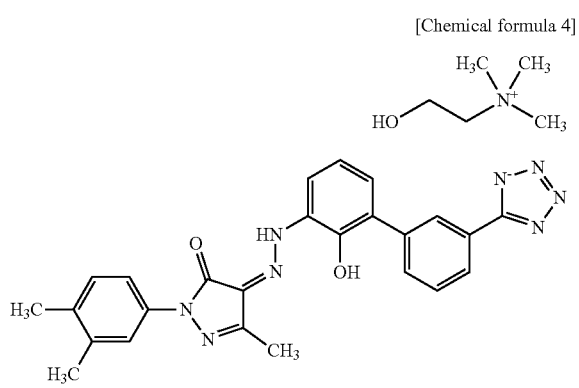

Romiplostim is a recombinant Fc-peptide fusion protein and includes the Fc region of human IgG1 from positions 2 to 228 in the amino acid sequence thereof and a human thrombopoietin receptor-binding sequence from positions 229 to 269. However, it does not have homology with the endogenous thrombopoietin. Romiplostim is a protein composed of two subunit each consisting of 269 amino acids.

Thrombocytopenia means a condition in which the number of platelets is decreased. A patient with thrombocytopenia means a patient having thrombocytopenia.

A pharmaceutical composition according to the present invention is a medicament for increasing platelets containing a compound having a thrombopoietin receptor agonistic activity, and is characterized by discontinuing administration of the pharmaceutical composition to a patient at the time point when the platelet count in the patient has increased by $2 \times 10^4 / \mu L$ or more from the platelet count before initiation of administration and has reached to $5 \times 10^4 / \mu L$ or higher.

Prior to initiation of administration of a pharmaceutical composition of the present invention, the platelet count in a patient is measured. The platelet count in a patient is measured over time after initiation of administration.

The phrase "a platelet count in the patient has increased by $2 \times 10^4 / \mu L$ or more from a platelet count before initiation of administration and has reached to $5 \times 10^4 / \mu L$ or higher" means the situation that the platelet count at a certain time point after initiation of administration has increased by $2 \times 10^4 / \mu L$ or more from the platelet count before initiation of administration and the platelet count at the same time point has reached to $5 \times 10^4 / \mu L$ or higher.

The term "platelet count before initiation of administration" means the platelet count before the first administration of a pharmaceutical composition of the present invention. It is desirable to determine the "platelet count before initiation of administration" within a short period before initiation of administration. For example, it is preferably determined within 7 days before initiation of administration and more preferably just before initiation of administration.

After initiation of administration, the platelet count is determined over time after a certain period of time from initiation of administration. For example, the platelet count may be determined over time after 3 days from initiation of administration.

The phrase "administration was discontinued" means that, administration of a pharmaceutical composition of the present invention is stopped, when it is confirmed that the platelet count in the patient increase by $2 \times 10^4 / \mu L$ or more from a platelet count before initiation of administration and reach $5 \times 10^4 / \mu L$ or higher in a determination of the platelet count after initiation of administration.

The term "maximum administration period" means a maximum period of time during which a pharmaceutical composition of the present invention is administered. For example, the maximum administration period of 7 days means that administration is carried out for 7 days to a patient who does not reach to the administration discontinuating criteria, and administration is discontinued at the time point to the patient who reaches the administration discontinuating criteria. The maximum administration period is preferably 14 days or less, more preferably 6 to 10 days and most preferably 7 days.

The term "pre-defined level of platelet count" in the present specification means a reference value of the platelet count that is required before an invasive procedure. If the platelet count is less than the pre-defined level of platelet count, treatment is required for increasing platelets such as platelet transfusion before carrying out invasive procedures in order to avoid the risk of bleeding. "$5 \times 10^4 / \mu L$" used in the administration discontinuating criteria is an embodiment of the "pre-defined level of platelet count". Examples of the pre-defined level of platelet count include any number selected from $4 \times 10^4$ to $6 \times 10^4 / \mu L$. The pre-defined level of platelet count is preferably a number selected from $4.5 \times 10^4$ to $5.5 \times 10^4 / \mu L$, more preferably a number selected from $4.8 \times 10^4$ to $5.2 \times 10^4 / \mu L$, still more preferably a number selected from $4.9 \times 10^4$ to $5.1 \times 10^4 / \mu L$ and most preferably $5 \times 10^4 / \mu L$.

The term "the pre-defined level of platelet count increment" in the present specification means a reference value that serves as a criterion as to how much increment from the platelet count before initiation of administration can be interpreted to indicate the tendency of increase in the platelet count in a patient who has a platelet count less than the pre-defined level of platelet count before invasive procedures when a compound having a thrombopoietin receptor agonistic activity is administered to the patient. "$2 \times 10^4 / \mu L$" used in the administration discontinuating criteria is an embodiment of the "pre-defined level of platelet count increment". The pre-defined level of platelet count increment is any number selected from $1.5 \times 10^4$ to $2.5 \times 10^4 / \mu L$, preferably a number selected from $1.8 \times 10^4$ to $2.2 \times 10^4 / \mu L$, more preferably $1.9 \times 10^4$ to $2.1 \times 10^4 / \mu L$ and still more preferably $2 \times 10^4 / \mu L$.

The term "invasive procedures" means procedures accompanied by bleeding.

The term "elective invasive procedures" means that, during the course of a disease, invasive procedures are carried out when the timing is suitable. The elective invasive procedures include various invasive procedures, particularly various minimally invasive procedures. Examples of minimally invasive procedures include local therapy, percutaneous needle biopsy, puncture of abscess, transcatheter arterial embolization (TAE), hepatic arterial chemotherapy (LipTAI), trancecatheter arterial chemoembolization (TACE), laparoscopy, endoscopic variceal ligation (EVL), endoscopic injection sclerotherapy (EIS), endoscopy with possible tissue biopsy, endoscopic submucosal dissection (ESD), endoscopic mucosal resection (EMR), polypectomy, endoscopic retrograde biliary drainage-expandable metallic stent (ERBD/EMS), endoscopic sphincterotomy (EST), percutaneous needle biopsy of organs (including endoscopic ultrasound-guided fine-needle aspiration (EUS-FNA)), various paracenteses, tooth extraction, transurethral resection of the prostate (TURP), transurethral resection of the bladder tumor (TUR-Bt), transurethral ureterolithotripsy (TUL), arthroscopy and the like.

Radiofrequency ablation (RFA) refers to a therapy in which coagulative necrosis of a lesion site is induced by high temperature generated by radio waves (frequency of around 500 kHz).

Chronic liver disease is a disease in which hepatocytes are damaged by persistent inflammation over a long period of time. Chronic liver disease gradually develops into liver cirrhosis and, in some cases, liver cancer. Examples of chronic liver disease include chronic liver disease caused by hepatitis B virus, chronic liver disease caused by hepatitis C virus, alcoholic chronic liver disease and non-alcoholic chronic steatohepatitis (NASH). In Japan, about 70% of chronic hepatitis cases are caused by hepatitis C and about 20% are caused by hepatitis B.

Examples of local therapy include therapies such as radiofrequency ablation (RFA), percutaneous ethanol injection therapy (PEIT) and microwave coagulation therapy (MCT).

The present invention is explained in more detail below by way of Examples and Test Examples, but is not limited the following Examples and Test Examples.

EXAMPLES

Example 1

Prediction of Profile of a Platelet Count by Monte-Carlo Simulation

An excessive increase in the platelet count is considered to increase a risk of thrombosis. In order to ensure the safety of patients who receive drugs, we designed an administration discontinuating criteria based on the platelet count. Using the data of pharmacokinetics and profile of a platelet count from single administration and repeated administration trials of lusutrombopag carried out to healthy adults, a profile of a platelet count during repeated administration of lusutrombopag for 7 days to chronic liver disease patients was predicted by Monte-Carlo simulation. In simulation, the PK/PD model parameters of healthy adults were estimated based on the data obtained from healthy adults (Test Example 1), and model parameters in chronic liver disease patients were calculated based on the PK/PD model in healthy adults (Test Example 2). Based on the calculated parameters, we verified the criteria in which administration of lusutrombopag is discontinued at the time point when the platelet count during administration period has increased by $2 \times 10^4/\mu L$ or more from the platelet count before initiation of administration and has reached to $5 \times 10^4/\mu L$ or higher (Test Example 3).

Test Example 1

Using the plasma concentration of the drug and the platelet count data of 54 cases obtained in phase 1 trial carried out in Japan to healthy male adults, a PK/PD model was constructed that can describe pharmacokinetics and a profile of a platelet count. The PK model describing pharmacokinetics was a three-compartment model including three compartments in the absorption process in order to explain the delay in absorption. The PD model describing the relation between the plasma concentration and the profile of platelets counts was a model including five compartments in order to explain the maturation process of platelets. FIG. 1 shows a schematic view of the PK/PD model with the mass balance equation thereof. Table 1 shows the PK/PD model parameters estimated from the data obtained from healthy adults. We assumed that the distributions of respective model parameters and the distributions of the residual errors of the models follow a log-normal distribution. Parameters were estimated by using the first order conditional estimation method with interaction in a software NONMEM (version VI, level 2.0).

TABLE 1

| PK parameter | Mean | Inter-individual variability (%) | PD parameter | Mean | Inter-individual variability (%) |
| --- | --- | --- | --- | --- | --- |
| CL (L/hr) | 0.776 | 17.6 | $E_{max}$ | 3.52 | — |
| V2/F (L) | 15.9 × (1 + (BW − 63) × 0.0172) | 18.0 | $EC_{50}$ (ng/mL) | | |
| Q3/F (L/hr) | 0.946 | — | <50 mg/dose | 64.7 | 50.0 |
| V3/F (L) | 6.28 | — | 50 mg/dose | 21.6 | 44.5 |
| Q4/F (L/hr) | 0.0262 | — | r | 2.03 | — |
| V4/F (L) | 2.71 | — | $k_m$ (hr$^{-1}$) | 0.0394 | 23.6 |
| $k_{tr}$ (hr$^{-1}$) | | | $k_{deg}$ (hr$^{-1}$) | 0.00578 | — |
| Fasting + solution | 4.19 | 67.2 | $PLT_0$ ($\times 10^4/\mu L$) | 20.1 | 16.1 |
| Postprandial + solution | 2.15 | 53.1 | γ | 0.309 | — |
| Postprandial + tablet | 1.38 | 41.8 | Intra-individual variability (%) | 5.71 | — |
| $k_a$ (hr$^{-1}$) | | | | | |
| Fasting + solution | 0.563 | 16.1 | | | |
| Postprandial + solution | 0.285 | 26.9 | | | |
| Postprandial + tablet | 0.854 | — | | | |

TABLE 1-continued

| PK parameter | Mean | Inter-individual variability (%) | PD parameter | Mean | Inter-individual variability (%) |
|---|---|---|---|---|---|
| Intra-individual variability (%) | 12.1 | — | | | |

(Explanations of Table 1)
CL/F: Apparent total clearance.
V2/F: Volume of distribution of the central compartment.
V3/F and V4/F: Volumes of distribution of peripheral compartments.
Q3/F and Q4/F: Inter-compartmental clearances.
$k_{tr}$: Inter-absorption-compartmental transfer rate constant.
$k_a$: Transfer rate constant from the absorption compartments to the central compartment.
$E_{max}$, $EC_{50}$ and r: parameters of a sigmoid $E_{max}$ model.
$k_m$: Inter-PD-compartmental transfer rate constant.
$k_{deg}$: Elimination rate constant from the platelet compartment.
$PLT_0$: Pre-defined level of platelet count.
γ: Feedback coefficient.
BW: Body weight (kg).
—: Not estimated.
$k_a$ and $k_{tr}$: Predictions were made depending on combinations of feeding status and dosage forms.
$EC_{50}$: Estimation were made depending on the doses of less than 50 mg/dose and 50 mg/dose.

Test Example 2

Estimation of PK/PD Parameters in Monte-Carlo Simulation

Based on the PK/PD model in healthy adults as described in (Test Example 1), model parameters in chronic liver disease patients were estimated on the basis of the following assumptions. Table 2 shows the estimated PK/PD model parameters used for platelet count predictions in chronic liver disease patients.

(Assumptions Used for the Estimation)
PK Parameters (CL, V2/F, Q2/F, V3/F, Q3/F, V4/F, Q4/F, $k_{tr}$ and $k_a$):

According to the results of phase 1 single administration clinical trial to patients with hepatic disorder classified into Child-Pugh classes A and B after administration of 0.75 mg of lusutrombopag, pharmacokinetics of lusutrombopag in patients with hepatic disorder were similar to those in healthy adults. Therefore, as PK parameters those from healthy adults were used. As parameters $k_a$ and $k_{tr}$, estimated values under the conditions of postprandial and tablets were used in line with clinical usage.

Pre-defined Level of Platelet Count ($PLT_0$):

Based on the pre-defined level of platelet count expected in chronic liver disease patients, the average and range of $PLT_0$ were set to $3 \times 10^4/\mu L$ and $2 \times 10^4$ to $4.9 \times 10^4/\mu L$, respectively.

Elimination Rate Constant From Platelet Compartment ($k_{deg}$):

It was reported that platelets destruction in chronic liver disease patients was promoted (see Reference 1) and the survival period of platelets was about ⅔ of that of healthy adults (see References 2 and 3). Therefore, $k_{deg}$, a parameter representing the elimination rate of platelets, was set to the value which was about 1.5 times of the value of healthy adults, i.e. 0.009 hr$^{-1}$. In addition, based on the relationship that the production rate of platelets is equal to the elimination rate of platelets at baseline, $k_{pr}$, a parameter representing the production rate of platelets, was calculated from the formula: $PLT_0 \times k_{deg}$. As a result, $k_{pr}$ was $0.027 \times 10^4/\mu L/hr$ which was lower than the value in healthy adults ($0.116 \times 10^4/\mu L/hr$). This estimated value matched the previous report that the production rate of platelets was decreased in chronic liver disease patients (see Reference 1).

Inter-PD-compartmental Transfer Rate Constant ($k_m$):

It was assumed that a parameter $k_m$ representing the maturation rate of platelets in chronic liver disease patients is similar to that in healthy adults. Therefore, the estimated value in healthy adults was used as $k_m$.

Parameters of a Sigmoid $E_{max}$ Model ($E_{max}$, $EC_{50}$ and r):

When the plasma concentration is sufficiently lower than $EC_{50}$ ($EC_{50} \gg C$), the drug efficacy of lusutrombopag can be approximated by $E_{max}/EC_{50}$. It was assumed based on the clinical data of eltrombopag, a drug having the same efficacy (see References 4 and 5) that $E_{max}/EC_{50}$ in this trial was about 3 times of the value of healthy adults. It was also assumed that the upper limit of platelets in the present model ($PLT_0 \times (1+E_{max})$) in chronic liver disease patients was similar to that in healthy adults and $E_{max}$ was set to 29.3 and $EC_{50}$ to 180 ng/mL. Meanwhile, it was assumed that r in the patients was similar to that in healthy adults. Therefore, the value in healthy adults was used as r.

Feedback Coefficient (γ):

A reduction in the production rate of platelets with an increase in platelets, i.e. the negative feedback phenomenon, is represented by the formula $(PLT_0/PLT)^\gamma$. It was assumed that it is a unique phenomenon for healthy adults having a normal platelet count level, and the negative feedback phenomenon does not occur in chronic liver disease patients having a decreased platelet baseline. Therefore, the negative feedback phenomenon was not taken into account in the present simulation.

Body Weight:

Body weight was assumed to follow normal distribution and the average was set to 60 kg, the coefficient of variation was set to 20%, and the range was set to 40 to 100 kg.

Inter-individual Variability of PD Model Parameters:

As inter-individual variability of the respective PD parameters, the values in healthy adults were used.

Intra-individual Variability of Plasma Concentration and a Platelet Count:

The intra-individual variability of plasma concentration was not taken into account in the present simulation. As the intra-individual variability of a platelet count, the value in healthy adults was used.

REFERENCES (Reference 1) Witters P, Freson K, Verslype C et al. Review article: blood platelet number and function in chronic liver disease and cirrhosis. Aliment Pharmacol Ther 2008; 27: 1017-1029.

(Reference 2) Harker L A, Finch C A. Thrombokinetics in man. J Clin Invest 1969; 48: 963-974.

(Reference 3) Aoki Y, Hirai K, Tanikawa K. Mechanism of thrombocytopenia in liver cirrhosis: kinetics of indium-111 tropolone labelled platelets. Eur J Nucl Med 1993; 20: 123-9.

(Reference 4) FDA application material (application No.: NDA 22-291).

(Reference 5) Data from GlaxoSimithKline (GSK study ID: 111913).

TABLE 2

| PK parameter | Mean | Inter-individual variability (%) | PD parameter | Mean | Inter-individual variability (%) |
|---|---|---|---|---|---|
| CL (L/hr) | 0.776 | 17.6 | $E_{max}$ | 29.3 | — |
| V2/F (L) | 15.9 × (1 + (BW − 63) × 0.0172) | 18.0 | $EC_{50}$ (ng/mL) | 180 | 50.0 |
| Q3/F (L/hr) | 0.946 | — | r | 2.03 | — |
| V3/F (L) | 6.28 | — | $k_m$ (hr$^{-1}$) | 0.0394 | 23.6 |
| Q4/F (L/hr) | 0.0262 | — | $k_{deg}$ (hr$^{-1}$) | 0.00900 | — |
| V4/F (L) | 2.71 | — | $PLT_0$ (×10$^4$/μL) | 3.00 | 16.1 |
| $k_{tr}$ (hr$^{-1}$) | 1.38 | 41.8 | Intra-individual variability (%) | 5.71 | |
| $k_a$ (hr$^{-1}$) | 0.854 | — | | — | — |

(Explanations of Table 2)
—: Not estimated.
BW (body weight): Body weight was assumed to follow normal distribution and the average was set to 60 kg, the coefficient of variation was set to 20%, and the range was set to 40 to 100 kg.
$PLT_0$: In the simulation, the range was set to 2.0 × 10$^4$ to 4.9 × 10$^4$/μL.

Test Example 3

In order to develop a method for reducing the risk of portal vein thrombosis, Monte-Carlo simulation was used to predict the following profile based on the parameters estimated in (Test Example 2) described above;

a profile of a platelet count in chronic liver disease patients repeatedly receiving 2 mg of lusutrombopag once daily for 7 days, and a profile of a platelet count in chronic liver disease patients repeatedly receiving 2 mg of lusutrombopag once daily for 7 days, provided that administration of lusutrombopag was discontinued at the time point when, during administration period, the platelet count has increased by 2×10$^4$/μL or more from a platelet count before initiation of administration and has reached to 5×10$^4$/μL or higher.

Monte-Carlo simulation was carried out with Trial Simulator software (version 2.2.1). Table 3 shows the following proportions which were calculated by the prediction;

the proportion of efficacy, i.e. the proportion of patients who had a platelet count on day 8 after initiation of administration that increased by 2×10$^4$/μL or more from a platelet count before initiation of administration and reached to 5×10$^4$/μL or higher, and the proportion of a thrombosis high-risk group, i.e. the proportion of patients who had the platelet count of higher than 20×10$^4$/μL during the observation period.

TABLE 3

| Administration discontinuating criteria[b] | Profile of platelet count | Proportion of patients (%) |
|---|---|---|
| No | Platelet count on day 8 after initiation of administration increased by 2 × 10$^4$/μL or more from a platelet count before initiation of administration and reached to 5 × 10$^4$/μL or higher | 92.4 |

TABLE 3-continued

| Administration discontinuating criteria[b] | Profile of platelet count | Proportion of patients (%) |
|---|---|---|
| | Platelet count during observation period exceeded $20 \times 10^4/\mu L$ | 35.8 |
| Yes | Platelet count on day 8 after initiation of administration increased by $2 \times 10^4/\mu L$ or more from a platelet count before initiation of administration and reached to $5 \times 10^4/\mu L$ or higher | 92.5 |
| | Platelet count during observation period exceeded $20 \times 10^4/\mu L$ | 11.7 |

(Explanations of Table 3)
Administration: at 2 mg, once daily for 7 days.
a) The efficacy and safety was estimated with Monte-Carlo simulation by predicting the platelet count over time of 1000 virtual patients with Monte-Carlo simulation and calculating the proportion of patients who had a platelet count on day 8 after initiation of administration that increased by $2 \times 10^4/\mu L$ or more from a platelet count before initiation of administration and reached to $5 \times 10^4/\mu L$ or higher and the proportion of patients who had the platelet count of higher than $20 \times 10^4/\mu L$ during the observation period (from initiation of administration to day 30 after initiation of administration).
[b]Administration discontinuating criteria: Administration of lusutrombopag was discontinued at the time point when the platelet count during administration has increased by $2 \times 10^4/\mu L$ or more from a platelet count before initiation of administration and has reached to $5 \times 10^4/\mu L$ or higher.

Without the administration discontinuating criteria, the estimated proportion of patients who had the platelet count on day 8 after initiation of administration that increased by $2 \times 10^4/\mu L$ or more from a platelet count before initiation of administration and reached to $5 \times 10^4/\mu L$ or higher was 92.4%. The estimated proportion of patients who had the platelet count of higher than $20 \times 10^4/\mu L$ during administration period was 35.8%. On the other hand, with the administration discontinuating criteria, the estimated proportion of patients who had the platelet count on day 8 after initiation of administration that increased by $2 \times 10^4/\mu L$ or more and reached to $5 \times 10^4/\mu L$ or higher was 92.5% which was similar to the proportion without the discontinuation criteria, while the estimated proportion of patients who had the platelet count of higher than $20 \times 10^4/\mu L$ during observation period was 11.7% which was lower than the proportion without the discontinuation criteria. Thus, the present simulation shows that the administration discontinuating criteria "administration of lusutrombopag is discontinued at the time point when the platelet count has increased by $2 \times 10^4/\mu L$ or more from a platelet count before initiation of administration and has reached to $5 \times 10^4/\mu L$ or higher" can reduce the proportion of patients who had a platelet count of higher than $20 \times 10^4/\mu L$ with almost no compromise on the efficacy, resulting in reduction of the risk of portal vein thrombosis.

Example 2

Test Example 1

To patients with thrombocytopenia caused by chronic liver disease, lusutrombopag as a pretreatment of percutaneous liver ablation was orally administered repeatedly for 7 days while applying the discontinuation criteria designed in Example 1 and profile of the platelet count was studied. In the present Example, the term "ablation" refers to radiofrequency ablation.
(Target Disease)
Patients with thrombocytopenia caused by chronic liver disease who are scheduled to undergo percutaneous liver ablation.
(Inclusion Criteria)
Patients who meet the following inclusion criteria are included.
1) Age: 20 years of age or older (at the time of signing informed consent);
2) Patients who themselves can give a consent in writing;
3) Patients who have a complication or a history of chronic liver disease caused by hepatitis B or C virus;
4) Patients who are scheduled to undergo percutaneous liver ablation for primary liver cancer;
5) Patients having a platelet count which is less than $5 \times 10^4/\mu L$ at the time of screening;
6) Patients whose ECOG* Performance Status of Grade is 0 to 1; and
7) Patients who can practice contraception from entry to the end of observation.
(Exclusion Criteria)
Patients who meet the following criteria are excluded.
1) Patients who underwent splenectomy;
2) Patients who have a complication presenting thrombocytopenia;
3) Patients who underwent liver transplant;
4) Degree of hepatic disorder classified as the Child-Pugh class of C;
5) Hepatic encephalopathy uncontrolled by medicaments;
6) Ascites uncontrolled by medicaments;
7) Patients who have a complication of malignant tumor other than primary liver cancer;
8) Patients who have a complication or a history of thrombosis or thrombotic disease;
9) Patients who have absence of hepatopetal blood flow in the portal vein;
10) Patients who have a complication or a history of disease with hemorrhage risk;
11) Patients who received a therapeutic agent that affects a platelet count or underwent a therapy that affects a platelet count within 90 days before registry;
12) Patients who received a blood product (excluding erythrocyte product) within 14 days before registry; or
13) Patients who previously received a TPO receptor agonist.
(Drugs which are Prohibited, Limited or Allowed for Coadministration During the Trial)
Drugs (therapies) which are prohibited, limited or allowed for coadministration during the trial are as follows:
(Drugs which are Prohibited for Coadministration)
The following drugs are prohibited from registry to the end of observation:
1) Blood products other than platelet and erythrocyte product such as whole blood products, human immunoglobulin products, blood coagulation factor products, fibrinogen, antithrombin III, fresh frozen plasma;
2) Anti-cancer drugs;
3) Interferon products;
4) Colony stimulation factor (G-CSF, M-CSF) products;
5) Erythropoietin;
6) TPO receptor agonists;
7) Antithrombotic drugs;
8) Hemostatic drugs such as carbazochrome sodium sulfate;
9) Vitamin K; or
10) Other investigational drugs.

(Schedule)

In each allocated group, lusutrombopag is orally administered repeatedly once daily for 7 days. After patients are monitored on day 8, they undergo percutaneous liver ablation before day 13 from initiation of administration. They are monitored until about day 30 after initiation of administration.

(Administration)

Lusutrombopag is orally administered repeatedly once daily for 7 days. On day 1, the drug is administered at the time of visit. On day 3 to day 7 (day 5 to day 7 for the group of 2.0 mg administration), the drug shall be administered after checking the platelet count measured on the same day. Administration of lusutrombopag shall be discontinued when the platelet count reaches to the following criteria (administration discontinuating criteria) in a clinical examination after administration of the investigational drug.

Administration discontinuating criteria: when the platelet count has increased by $2\times10^4/\mu L$ or more from the platelet count before initiation of administration and the platelet count has reached to $5\times10^4/\mu L$ or higher.

As the platelet count before initiation of administration, the platelet count determined within 7 days before initiation of administration was used.

(Dose)

Daily dose was any one of 2.0, 2.5, 3.0 and 4.0 mg of lusutrombopag.

(Endpoints)

Endpoint 1

Proportion of patients who have a platelet count on day 8 after initiation of administration that increased by $2\times10^4/\mu L$ or more from the platelet count before initiation of administration and reached to $5\times10^4/\mu L$ or higher.

Endpoint 2

1) Proportion of patients who received platelet transfusion and the number and dose (units) of the transfusion;
2) Proportion of patients who have a platelet count during the observation period that increases by $2\times10^4/\mu L$ or more from the platelet count before initiation of administration and reaches to $5\times10^4/\mu L$ or higher;
3) Platelet count;
4) Number of adverse events relating to hemorrhage;
5) Number of adverse events relating to thrombosis;
6) Number of adverse events and side effects; and
7) Plasma concentration of the unchanged drug.

(Results)

Data relating to the efficacy at each dose are shown in Table 4. The profile of the platelet count in each patient at the daily dose of 2.0 mg, 2.5 mg, 3.0 mg and 4.0 mg of lusutrombopag is shown in FIGS. 2 to 5, respectively. It was confirmed that all doses showed the efficacy. None of the patients in any trials had a platelet count of higher than $20\times10^4/\mu L$ during the observation period. Particularly, the patients in the groups of the daily dose of 2 mg, 2.5 mg and 4.0 mg to whom administration was discontinued according to the administration discontinuating criteria of the present invention showed the following; "the platelet count increased over a certain period after discontinuation of administration, and the maximum platelet count was lower than that of patients who received the drug for 7 days". It is believed that by discontinuing administration of the drug according to the administration discontinuating criteria of the present invention, an excessive increase of platelets could be prevented. The results of the present trial demonstrated that the administration discontinuating criteria of the present invention is superior in that the criteria can ensure the sufficient platelet count while preventing an excessive increase in the platelet count.

TABLE 4

| | | Lusutrombopag (mg, once daily) | | | |
|---|---|---|---|---|---|
| | | 2.0 n = 12 | 2.5 n = 6 | 3.0 n = 7 | 4.0 n = 8 |
| Endpoint 1 | Number (proportion, %) of patients who had a platelet count on day 8 after initiation of administration that increased by $2 \times 10^4/\mu L$ or more from the count before initiation of administration and reached to $5 \times 10^4/\mu L$ or higher | 4 (33.3) | 4 (66.7) | 3 (42.9) | 4 (50.0) |
| Endpoint 2 | Number (proportion, %) of patients who had a platelet count during the trial that increased by $2 \times 10^4/\mu L$ or more from the count before initiation of administration and reached to $5 \times 10^4/\mu L$ or higher | 9 (75.0) | 4 (66.7) | 6 (85.7) | 7 (87.5) |
| | Number of patients who received platelet transfusion | 2 | 1 | 1 | 1 |

TABLE 4-continued

|  |  | Lusutrombopag (mg, once daily) | | | |
| --- | --- | --- | --- | --- | --- |
|  |  | 2.0 n = 12 | 2.5 n = 6 | 3.0 n = 7 | 4.0 n = 8 |
| Discontinuation according to the administration discontinuating criteria[a)] | Number of patients to whom administration was discontinued according to the administration discontinuating criteria | 3 | 3 | 0 | 2 |
|  | Day(s) of administration 1 day | 0 | 0 | 0 | 0 |
|  | 2 days | 0 | 0 | 0 | 1 |
|  | 3 days | 0 | 0 | 0 | 0 |
|  | 4 days | 0 | 0 | 0 | 1 |
|  | 5 days | 2 | 1 | 0 | 0 |
|  | 6 days | 1 | 2 | 0 | 0 |

(Explanations of Table 4)
[a)]Administration discontinuating criteria: Administration of lusutrombopag was discontinued at the time point when the platelet count during administration period has increased by $2 \times 10^4/\mu L$, or more from the platelet count before initiation of administration and has reached to $5 \times 10^4/\mu L$, or higher.

Test Example 2

To patients with thrombocytopenia caused by chronic liver disease, lusutrombopag as a pretreatment of percutaneous liver ablation was orally administered repeatedly for 7 days while applying the discontinuation criteria designed in Example 1 and profile of the platelet count was studied. In the present Example, the term "ablation" refers to radiofrequency ablation.

(Target Disease)

Patients with thrombocytopenia caused by chronic liver disease who are scheduled to undergo percutaneous liver ablation.

(Inclusion Criteria)

Patients who meet the following inclusion criteria are included.
1) Age: 20 years of age or older (at the time of consent);
2) Patients who themselves can give a consent in writing;
3) Patients with thrombocytopenia caused by chronic liver disease;
4) Patients who are scheduled to undergo percutaneous liver ablation for primary liver cancer;
5) Patients having a platelet count which is less than $5 \times 10^4/\mu L$ at the time of screening;
6) Patients whose ECOG* Performance Status of Grade is 0 to 1; and
7) Patients who can practice contraception from entry to the end of observation.

(Exclusion Criteria)

Patients who meet the following criteria are excluded.
1) Patients who underwent splenectomy;
2) Patients who have a complication presenting thrombocytopenia;
3) Patients who underwent liver transplant;
4) Degree of hepatic disorder classified as the Child-Pugh class of C;
5) Hepatic encephalopathy uncontrolled by medicaments;
6) Ascites uncontrolled by medicaments;
7) Patients who have a complication of malignant tumor other than primary liver cancer;
8) Patients who have a complication or a history of thrombosis or thrombotic disease;
9) Patients who have absence of hepatopetal blood flow in the portal vein;
10) Patients who have a complication or a history of disease with hemorrhage risk;
11) Patients who received a therapeutic agent that affects a platelet count or underwent a therapy that affects a platelet count within 90 days before registry;
12) Patients who received a blood product (excluding erythrocyte product) within 14 days before registry; or
13) Patients who previously received a TPO receptor agonist.

(Drugs which are Prohibited, Limited or Allowed for Coadministration During the Trial)

Drugs (therapies) which are prohibited, limited or allowed for coadministration during the trial are as follows:

(Drugs which are Prohibited for Coadministration)

The following drugs are prohibited from registry to the end of observation:
1) Blood products other than platelet and erythrocyte products such as whole blood products, human immunoglobulin products, blood coagulation factor products, fibrinogen, antithrombin III, fresh frozen plasma;
2) Anti-cancer drugs;
3) Interferon products;
4) Colony stimulation factor (G-CSF, M-CSF) products;
5) Erythropoietin;
6) TPO receptor agonists;
7) Antithrombotic drugs;
8) Hemostatic drugs such as carbazochrome sodium sulfate;
9) Vitamin K; or
10) Other investigational drugs.

(Schedule)

In each allocated group, lusutrombopag is orally administered repeatedly once daily for 7 days. After patients are monitored on day 8, they undergo percutaneous liver ablation before day 14 from initiation of administration. They are monitored until about day 30 after initiation of administration.

(Administration)

Lusutrombopag is orally administered repeatedly once daily for 7 days. On day 1, the drug is administered at the time of visit. On day 5 to day 7, the drug shall be administered after checking the platelet count measured on the same day. Administration of lusutrombopag shall be discontinued when the platelet count reaches to the following criteria (administration discontinuating criteria) in a clinical examination after administration of the investigational drug.

Administration discontinuating criteria: when the platelet count has increased by $2 \times 10^4/\mu L$ or more from the platelet count before initiation of administration and the platelet count has reached to $5 \times 10^4/\mu L$ or higher.

As the platelet count before initiation of administration, the platelet count determined within 7 days before initiation of administration was used.

(Dose)
Daily dose was any one of 2.0, 3.0 and 4.0 mg of lusutrombopag.
(Endpoints)
Endpoint 1
Proportion of patients who have a platelet count on day 8 after initiation of administration that increased by $2\times10^4/\mu L$ or more from a platelet count before initiation of administration and reached to $5\times10^4/\mu L$ or higher.
Endpoint 2
1) Proportion of patients who received platelet transfusion and the number and dose (units) of the transfusion;
2) Proportion of patients who have a platelet count during the observation period that increases by $2\times10^4/\mu L$ or more from the platelet count before initiation of administration and reaches to $5\times10^4/\mu L$ or higher;
3) Platelet count;
4) Number of adverse events relating to hemorrhage;
5) Number of adverse events relating to thrombosis;
6) Number of adverse events and side effects; and
7) Plasma concentration of the unchanged drug.
(Results)
Data relating to the efficacy at each dose are shown in Table 5. It was confirmed that all doses showed the efficacy. None of the patients in any trials had a platelet count of higher than $20\times10^4/\mu L$, during the observation period. The results of the present trial demonstrated that the administration discontinuating criteria of the present invention is superior in that the criteria can ensure the sufficient platelet count while preventing an excessive increase in the platelet count.

FORMULATION EXAMPLES

The following Formulation Examples are only exemplified and not intended to limit the scope of the invention.

Formulation Example 1

Tablets

| | |
|---|---|
| Compound of the present invention | 15 mg |
| Lactose | 15 mg |
| Calcium stearate | 3 mg |

The components other than calcium stearate are homogeneously mixed, and the mixture is ground, granulated and dried to obtain an appropriate size of granules. Then, calcium stearate is added thereto and the mixture is compressed to obtain tablets.

Formulation Example 2

Capsules

| | |
|---|---|
| Compound of the present invention | 10 mg |
| Magnesium stearate | 10 mg |
| Lactose | 80 mg |

TABLE 5

| | | Lusutrombopag (mg, once daily) | | | |
|---|---|---|---|---|---|
| | | Placebo n = 15 | 2.0 n = 15 | 3.0 n = 16 | 4.0 n = 15 |
| Endpoint 1 | Number (proportion, %) of patients who had a platelet count on day 8 after initiation of administration that increased by $2 \times 10^4/\mu L$ or more from the count before initiation of administration and reached to $5 \times 10^4/\mu L$ or higher | 0 (0.0) | 6 (40.0) | 5 (33.3) | 8 (53.3) |
| Endpoint 2 | Number (proportion, %) of patients who had a platelet count during the trial that increased by $2 \times 10^4/\mu L$ or more from the count before initiation of administration and reached to $5 \times 10^4/\mu L$ or higher | 1 (6.7) | 10 (66.7) | 11 (68.8) | 12 (80.0) |
| | Number of patients who received platelet transfusion | 12 | 3 | 3 | 4 |
| Discontinuation according to the administration discontinuating criteria[a] | Number of patients to whom administration was discontinued according to the administration discontinuating criteria | 0 | 3 | 3 | 5 |
| Day(s) of administration | 1 day | 0 | 0 | 0 | 0 |
| | 2 days | 0 | 0 | 0 | 0 |
| | 3 days | 0 | 0 | 0 | 0 |
| | 4 days | 0 | 0 | 1 | 1 |
| | 5 days | 0 | 1 | 2 | 0 |
| | 6 days | 0 | 2 | 0 | 4 |

(Explanations of Table 5)
[a] Administration discontinuating criteria: Administration of lusutrombopag was discontinued at the time point when the platelet count during administration period has increased by $2 \times 10^4/\mu L$ or more from the platelet count before initiation of administration and has reached to $5 \times 10^4/\mu L$ or higher.

The above components are homogeneously mixed to obtain powder or fine granules. Then, the powder medicines are encapsulated in capsule shells to obtain capsules.

Formulation Example 3

Granules

| | |
|---|---|
| Compound of the present invention | 30 g |
| Lactose | 265 g |
| Magnesium stearate | 5 g |

The above components are thoroughly mixed, and the mixture is compressed and molded. Then, it is ground, granulated and sieved to obtain an appropriate size of granules.

INDUSTRIAL APPLICABILITY

It is believed that the pharmaceutical composition having a thrombopoietin receptor agonistic activity according to the present invention is useful because it can increase platelets while avoiding a risk of thrombosis caused by an excessive increase in the platelet count.

The invention claimed is:

1. A method for increasing platelets comprising steps of: administering a pharmaceutical composition comprising (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof to a patient, and discontinuing administering the pharmaceutical composition when a platelet count in the patient has increased by $1.5 \times 10^4$ to $3.0 \times 10^4/\mu L$ from the platelet count before initiation of the administering and has reached $5.0 \times 10^4$ to $7.8 \times 10^4/\mu L$, wherein the platelet count before initiation of the administering is less than $5 \times 10^4/\mu L$.

2. The method for increasing platelets according to claim 1,
wherein the patient has thrombocytopenia.

3. The method for increasing platelets according to claim 2,
wherein the patient to whom the pharmaceutical composition is administered is scheduled to undergo an invasive procedure.

4. The method for increasing platelets according to claim 3,
wherein the invasive procedure is an elective invasive procedure.

5. The method for increasing platelets according to claim 3,
wherein the invasive procedure is radiofrequency ablation.

6. The method for increasing platelets according to claim 5,
wherein the radiofrequency ablation is performed on liver cancer.

7. The method for increasing platelets according to claim 6,
wherein the liver cancer is primary liver cancer.

8. The method for increasing platelets according to claim 1,
wherein the patient has a chronic liver disease.

9. The method for increasing platelets according to claim 8,
wherein the chronic liver disease is caused by hepatitis B virus or hepatitis C virus.

10. The method for increasing platelets according to claim 1, wherein the pharmaceutical composition is orally administered.

11. The method for increasing platelets according to claim 10,
wherein the pharmaceutical composition is administered in a range from 2.0 to 4.0 mg/day as an amount of (E)-3-[2,6-dichloro-4-[4-[3-[(S)-1-hexyloxyethyl]-2-methoxyphenyl]-thiazol-2-ylcarbamoyl]-phenyl]-2-methylacrylic acid or a salt thereof.

12. The method for increasing platelets according to claim 11,
wherein a maximum period for the administering the pharmaceutical composition with once daily administration is 14 days or less.

13. The method for increasing platelets according to claim 1, which promotes production of platelets before invasive procedures in the patient, who is a thrombocytopenic patient having a chronic liver disease.

14. The method for increasing platelets according to claim 1, which promotes production of platelets before elective invasive procedures in the patient, who is a thrombocytopenic patient having a chronic liver disease.

15. The method for increasing platelets according to claim 1, which promotes production of platelets before local therapy for primary liver cancer.

16. The method for increasing platelets according to claim 1, which promotes production of platelets before radiofrequency ablation for primary liver cancer.

17. The method for increasing platelets according to claim 1, which promotes production of platelets before various minimally invasive procedures in the patient, who is a thrombocytopenic patient having a chronic liver disease.

* * * * *